US00PP37558P2

(12) United States Plant Patent
Kitajima

(10) Patent No.: US PP37,558 P2
(45) Date of Patent: Aug. 4, 2026

(54) ***CATHARANTHUS* PLANT NAMED 'Kchuchu4'**

(50) Latin Name: *Catharanthus roseus*
Varietal Denomination: Kchuchu4

(71) Applicant: Osamu Kitajima, Sakurai (JP)

(72) Inventor: Osamu Kitajima, Sakurai (JP)

( * ) Notice: Subject to any disclaimer, the term of this patent is extended or adjusted under 35 U.S.C. 154(b) by 0 days.

(21) Appl. No.: 19/436,399

(22) Filed: Dec. 30, 2025

(51) Int. Cl.
*A01H 5/02* (2018.01)
*A01H 6/08* (2018.01)

(52) U.S. Cl.
USPC ..... Plt./263.1
CPC ..... *A01H 6/084* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Catharanthus* plant named 'Kchuchu4', characterized by its compact, upright to somewhat outwardly spreading plant habit; vigorous growth habit; freely basal branching habit; freely flowering habit; and frilled purplish pink-colored flower petals with lighter purplish pink to white-colored margins.

2 Drawing Sheets

Figure 1:
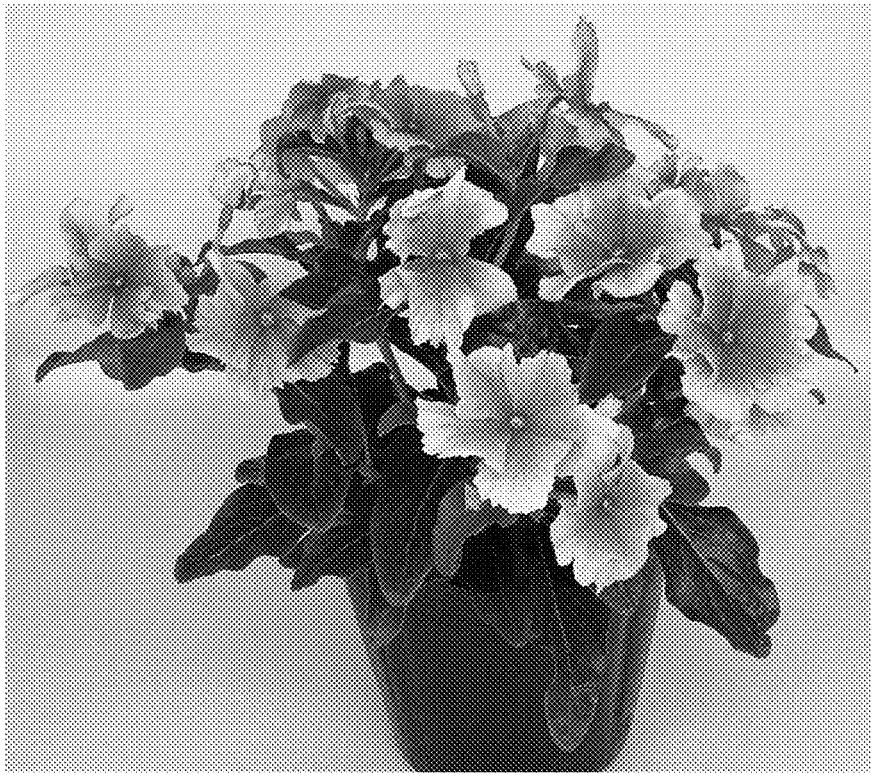

Botanical designation: *Catharanthus roseus.*
Cultivar denomination: 'KCHUCHU4'.

BACKGROUND OF THE INVENTION

The present invention relates to a new and distinct *Catharanthus* plant, botanically known as *Catharanthus roseus,* commonly referred to as Periwinkle and hereinafter referred to by the cultivar name 'Kchuchu4'.

The new *Catharanthus* plant is a product of a planned breeding program conducted by the Inventor in Sakurai, Nara, Japan. The objective of the breeding program is to develop new upright and freely branching *Catharanthus* plants with attractive frilled flowers.

The new *Catharanthus* plant originated from a cross-pollination in Sakurai, Nara, Japan conducted by the Inventor in July 2018 of a proprietary selection of *Catharanthus roseus* identified as code designation PCHUCHU, not patented, as the female, or seed, parent with a proprietary selection of *Catharanthus roseus* identified as code designation ECHUCHU, not patented, as the male, or pollen, parent. The new *Catharanthus* plant was discovered and selected by the Inventor as a single flowering plant from within the progeny of the stated cross-pollination in a controlled greenhouse environment in Sakurai, Nara, Japan in May 2019.

Asexual reproduction of the new *Catharanthus* plant by vegetative tip cuttings in a controlled greenhouse environment in Sakurai, Nara, Japan since May 2019, has shown that the unique features of this new *Catharanthus* plant are stable and reproduced true to type in successive generations.

SUMMARY OF THE INVENTION

Plants of the new *Catharanthus* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'Kchuchu4'. These characteristics in combination distinguish 'Kchuchu4' as a new and distinct *Catharanthus* plant:

1. Compact, upright to somewhat outwardly spreading plant habit.
2. Vigorous growth habit.
3. Freely basal branching habit.
4. Freely flowering habit.
5. Frilled purplish pink-colored flower petals with lighter purplish pink to white-colored margins.

Plants of the new *Catharanthus* can be compared to plants of the female parent selection. Plants of the new *Catharanthus* differ primarily from plants of the female parent selection in flower petal margins as petal margins of plants of the new *Catharanthus* are undulate or frilled whereas flower petals of plants of the female parent selection are not undulate or frilled. In addition, flower petals of plants of the new *Catharanthus* are purplish pink in color with lighter purplish pink to white-colored margins whereas flower petals of plants of the female parent selection are white in color with dark red-colored bases.

Plants of the new *Catharanthus* can be compared to plants of the male parent selection. Plants of the new *Catharanthus* differ primarily from plants of the male parent selection in flower color as flower petals of plants of the new *Catharanthus* are purplish pink in color with lighter purplish pink to white-colored margins whereas flower petals of plants of the male parent selection are white in color with light pink-colored bases.

Plants of the new *Catharanthus* can be compared to plants of the *Catharanthus roseus* 'Sunnichitaro', disclosed in U.S. Plant Pat. No. 25,112. In side-by-side comparisons, plants of the new *Catharanthus* differ from plants of 'Sunnichitaro' in the following characteristics:

1. Plants of the new *Catharanthus* are more compact than and not as broad as plants of 'Sunnichitaro'.
2. Plants of the new *Catharanthus* have smaller flowers than plants of 'Sunnichitaro'.

3. Plants of the new *Catharanthus* and 'Sunnichitaro' differ in flower color as flower petals of plants of the new *Catharanthus* are purplish pink in color with lighter purplish pink to white-colored margins whereas flower petals of plants of 'Sunnichitaro' are light red purple in color with darker red purple-colored bases.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph on the first sheet (FIG. 1) is a side perspective view of a typical flowering plant of 'Kchuchu4' grown in a container.

Figure 2:
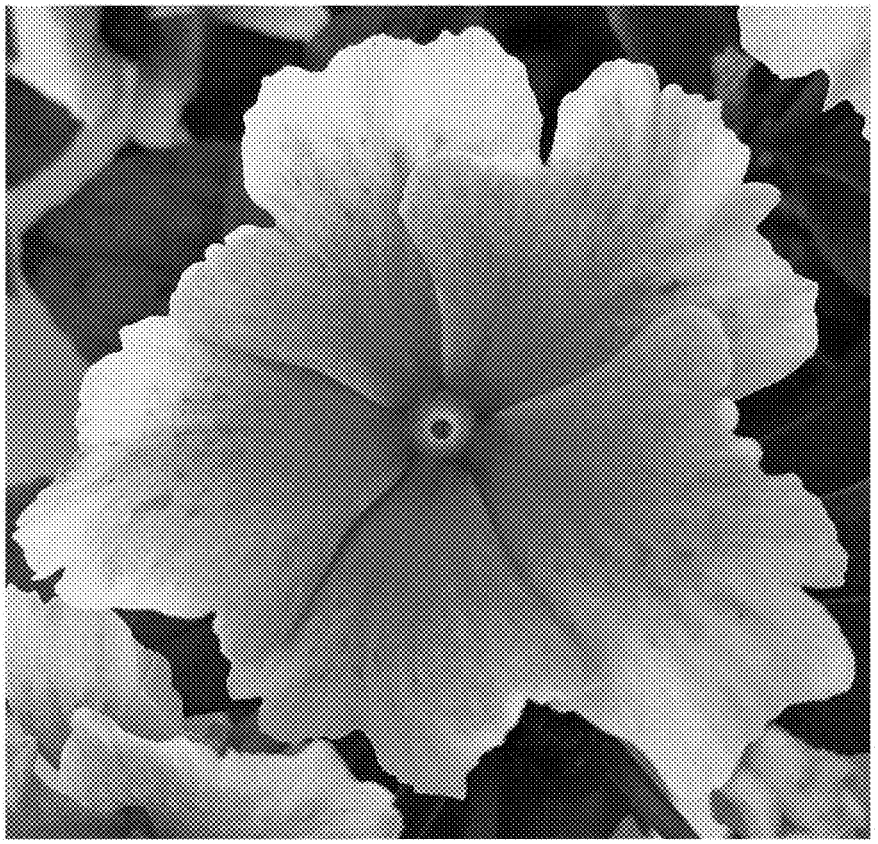

The photograph on the second sheet (FIG. 2) is a close-up view of a typical flower of 'Kchuchu4'.

DETAILED BOTANICAL DESCRIPTION

The aforementioned photographs and following observations, measurements and values describe plants grown during the late spring/early summer in 24-cm containers in an outdoor nursery in Higashiomi, Shiga, Japan and under cultural practices typical of commercial *Catharanthus* production. During the production of the plants, day temperatures averaged 25° C. and night temperatures averaged 15° C. Plants were four months old when the photographs and the description were taken. In the following description, color references are made to The Royal Horticultural Society Colour Chart, 2015 Edition, except where general terms of ordinary dictionary significance are used.

Botanical classification: *Catharanthus roseus* 'Kchuchu4'.

Parentage:

*Female, or seed, parent*.—Proprietary selection of *Catharanthus roseus* identified as code designation PCHUCHU, not patented.

*Male, or pollen, parent*.—Proprietary selection of *Catharanthus roseus* identified as code designation ECHUCHU, not patented.

Propagation:

*Type*.—By vegetative tip cuttings.

*Time to initiate roots, summer*.—About two weeks at temperatures about 30° C.

*Time to initiate roots, winter*.—About three weeks at temperatures about 25° C.

*Time to produce a rooted young plant, summer*.—About five weeks at temperatures about 30° C.

*Time to produce a rooted young plant, winter*.—About six weeks at temperatures about 25° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, upright to somewhat outwardly spreading plant habit; freely basal branching habit, about six basal branches develop per plant; pinching is typically not required; vigorous growth habit.

*Plant height*.—About 21.8 cm.

*Plant diameter*.—About 27.3 cm.

Lateral branch description:

*Length*.—About 15.8 cm.

*Diameter*.—About 2.5 mm.

*Internode length*.—About 2.2 cm.

*Aspect*.—Mostly upright to somewhat outwardly spreading.

*Texture*.—Rough, sparsely pubescent.

*Color*.—Close to 145B.

Leaf description:

*Quantity of leaves per lateral branch*.—About 13.

*Arrangement*.—Opposite, simple.

*Length*.—About 6.9 cm.

*Width*.—About 3.2 cm.

*Shape*.—Elliptic.

*Apex*.—Broadly acute.

*Base*.—Attenuate.

*Margin*.—Entire; undulate.

*Texture, upper and lower surfaces*.—Rough, sparsely pubescent.

*Venation pattern*.—Pinnate; reticulate.

*Color*.—Developing leaves, upper surface: Close to 143A. Developing leaves, lower surface: Close to 143B. Fully expanded leaves, upper surface: Close to 138A; venation, close to 145B. Fully expanded leaves, lower surface: Close to 138B; venation, close to 145C.

*Petioles*.—Length: About 3.2 mm. Diameter: About 2.4 mm. Texture, upper and lower surfaces: Rough, sparsely pubescent. Color, upper and lower surfaces: Close to 145B.

Flower description:

*Flower arrangement and habit*.—Single-type star-shaped flowers arising from upper leaf axils; freely flowering habit with about six flowers per lateral branch and numerous flowers per plant developing during the flowering season; flowers face mostly upright to slightly outwardly.

*Fragrance*.—None detected.

*Flowering habit*.—Plants begin flowering about two to three weeks after planting rooted young plants; long flowering period, in the garden, plants flower continuously from the early summer to late autumn in Japan.

*Flower longevity*.—Individual flowers last about two to three days on the plant; flowers not persistent.

*Flower buds*.—Length: About 4 cm. Diameter: About 7.2 mm. Shape: Ovoid to cylindrical. Color: Close to 150D.

*Flower diameter*.—About 4 cm.

*Flower length (depth)*.—About 3.6 cm.

*Corolla tube (outside) diameter*.—Proximally, about 1.8 mm; distally, about 2.8 mm.

*Corolla tube (outside) length*.—About 2.7 cm.

*Corolla*.—Arrangement: Five petals in a single whorl and fused at the base into a slender tube; petals imbricate. Petal length from throat: About 2.2 cm. Petal width: About 2.2 cm. Petal shape: Broadly obovate to transversely elliptic; asymmetrical. Petal apex: Broadly acute; emarginate. Petal base: Fused to corolla tube. Petal margin: Emarginate or incised; undulate or frilled. Petal texture, upper and lower surfaces: Smooth, glabrous. Corolla throat (inside) texture: Smooth, glabrous. Corolla tube (outside)

texture: Rough, pubescent. Color: Petals, when opening, upper surface: Close to 63C; towards the margins, close to 63D. Petals, when opening, lower surface: Close to 150D. Petals, fully opened, upper surface: Close to 63C; towards the margins, close to 63D and NN155D; towards the base, close to 63B. Petals, fully opened, lower surface: Close to 158C. Corolla throat (inside): Proximally, close to 145C; distally, close to 145B. Corolla tube (outside): Proximally, close to 145B; distally, close to 145A.

*Calyx*.—Arrangement: Star-shaped calyx with five sepals fused towards the base and curled outwardly towards the apex. Sepal length: About 2 mm. Sepal width: About 1.1 mm. Sepal shape: Lanceolate. Sepal apex: Acute. Sepal margin: Entire. Sepal texture, upper and lower surfaces: Rough, sparsely pubescent. Color, upper surface: Close to 138B. Color, lower surface: Close to 138A.

*Peduncles*.—Length: About 2 mm. Diameter: About 1.4 mm. Angle: Upright to outwardly. Texture: Rough, sparsely pubescent. Color: Close to 145B.

*Reproductive organs*.—Stamens: Quantity per flower: Five; filaments fused to the corolla tube. Anther size: About 1 mm by 2 mm. Anther shape: Narrowly elliptic. Anther color: Close to 150D. Pollen amount: Sparse. Pollen color: Close to 150D. Pistils: To date, pistil development has not been observed on plants of the new *Catharanthus*. Seeds and fruits: To date, seed and fruit development have not been observed on plants of the new *Catharanthus*.

Temperature tolerance: Plants of the new *Catharanthus* have been observed to tolerate temperatures ranging from about 5° C. to about 35° C. to 40° C.

Pathogen & pest resistance: To date, plants of the new *Catharanthus* have not been observed to be resistant to pathogens and pests common to *Catharanthus* plants.

It is claimed:

1. A new and distinct *Catharanthus* plant named 'Kchuchu4' as herein illustrated and described.

* * * * *